United States Patent [19]

Stephan

[11] 4,153,683

[45] May 8, 1979

[54] GALENIC IMMUNE-GLOBULIN PREPARATION

[75] Inventor: Wolfgang Stephan, Dreieich, Fed. Rep. of Germany

[73] Assignee: Biotest-Serum-Institut GmbH, Frankfurt, Fed. Rep. of Germany

[21] Appl. No.: 776,672

[22] Filed: Mar. 11, 1977

[30] Foreign Application Priority Data

Mar. 15, 1976 [DE] Fed. Rep. of Germany ....... 2610854

[51] Int. Cl.² ................ A61K 39/00; A61K 39/40; A61K 39/42
[52] U.S. Cl. ................................ 424/85; 424/86; 424/87
[58] Field of Search .............. 424/85, 86, 87, 101; 260/112 B

[56] References Cited

U.S. PATENT DOCUMENTS

| | | | |
|---|---|---|---|
| 3,452,135 | 6/1969 | Medveczky | 424/9 |
| 3,607,858 | 9/1971 | Querry et al. | 260/112 B |
| 3,928,580 | 12/1975 | Fontaine | 260/112 B |
| 3,966,906 | 6/1976 | Schultze et al. | 424/85 |

FOREIGN PATENT DOCUMENTS 550833  5/1932  Fed. Rep. of Germany ............. 424/88
25675 of  1910  United Kingdom ...................... 424/93

OTHER PUBLICATIONS

Biochem. Pharmacol., 22 (22), 1973, 2911–2917, "Anti--Viral Effect of Human J. Globulin in Mice:Comparison Between the Efficacy of Local and Systemic Administration."
Medveczky, E., Chem. Abstracts 66:5773k (1967).
Medveczky, E., Chem. Abstracts, 69:109829c (1968).

*Primary Examiner*—Donald G. Daus
*Assistant Examiner*—M. C. Eakin
*Attorney, Agent, or Firm*—Sprung, Felfe, Horn, Lynch & Kramer

[57] ABSTRACT

A galenic immune-globulin preparation for the treatment of skin viruses, fungus and bacterial diseases, comprising about 1 to 30% by weight of immune-globulin prepared from human blood, and a carrier. The immune-globulin may be a standard gamma globulin, a chemically stabilized or an enzymatically or hydrolytically decomposed immuneglobulin, non-fractionated serum, etc., and the composition may be a salve with a conventional base.

9 Claims, No Drawings

GALENIC IMMUNE-GLOBULIN PREPARATION

The invention concerns a galenic immune globulin preparation for combating skin diseases of various origins.

The use of immune-globulins prepared from human blood for the prophylaxis and therapy of infectious diseases is known. Through intramuscular or intravenous injections the missing antibodies are supplied in liquid form to the organism which is sick or is to be protected, which disperse throughout the entire organism and intercept infiltrating pathogenic agents. When using human antibodies one avoids an immunization such as would result in case of the parenteral administration of animal antibodies so that one can administer larger amounts of antibodies repeatedly. Thus it is possible, for example, to supply a person with 5 g per 100 ml immune-globulins through intravenous injection within twenty-four hours. Because of the distribution of the antibodies over the entire organism there results, however, a dilution of about 1:100 so that the end concentration of administered immune-globulin is relatively small. For this reason, numerous diseases such as, for instance, fungus diseases of the skin and of organs, as well as virus diseases of the skin or of the eye, do not respond at all to the conventional immune-globulin therapy, or only poorly.

It has now been discovered that the antibody concentration can be increased at the diseased point of the organism by a factor of 100 if one selects a local form of application instead of the parenteral application form of the antibodies.

The subject matter of the invention is a galenic immune-globulin preparation which is characterized in that it contains as active substance immune-globulin prepared from human blood.

The immune globulin can be a standard gammaglobulin, a chemically stabilized or an enzymatically or hydrolytically decomposed immune-globulin. All of these products are known from the following literature:

Stephan, W., Vox, Sanguinis 28 (1975) pp. 422–437

Schultze, H. E., and Schwick, G., Deutsche Medizinische

Wochenschrift [German medical weekly] 87 (1962) pp. 1643–1650

Barandun, S. et al., Vox Sanguinis 28 (1975) pp. 157–175

Barandun, S. et al., Vox Sanguinis 7 (1962) p. 157

Kistler, P. and Nitschmann, H. S., Vox Sanguinis 7 (1962), pp. 414–424.

Non-fractionated serum can also be used advantageously, which contains the immune-globulin types: IgG, IgA and IgM, the mucous membrane-protecting IgA being of special interest in connection with the invention.

The use of products decomposed enzymatically or hydrolytically is especially advantageous because such immune-globulins have an especially small molecule size and, therefore, can better penetrate into the skin.

The preparations according to the invention are effective against a broad spectrum of provocative agents from the group of the viruses, bacteria and fungi in the infected areas, for example against the viruses: mastoid virus, Herpes-simplex virus, Herpes-zoster virus; the bacteria: E. coli, pseudomonas, streptococci, staphylococci and the fungi species: Candida, trichophyton, microsporum, epidermophyton, aspergillus.

The application of the preparations according to the invention can take place in the form of ointments, creams, foams, tablets, powders, suppositories, dry sprays, milks, lotions, solutions or other possible pharmaceutical forms of application permitting an external or local treatment. The immune-globulins can, for instance, also be an ingredient of plasters or bandages.

In addition to the active substance according to the invention, such medical preparations can in some cases also contain other known agents for the disease to be combated such as, for instance, cortisones, antibiotics and the like.

Depending on the nature of the desired preparation, all respectively suitable and pharmaceutically permissible auxiliary agents which do not destroy the activity of the active substance are suitable as carrier materials. For creams there may be used stearates such as glycerine stearate or ethylene glycol stearate, fatty alcohols such as stearyl alcohol, cetyl alcohol or cetyl stearyl alcohol and vegetable or mineral oils such as vaseline oil, paraffins, olive oil, soy oil. Fatty acids can also be added.

In all cases it must, however, only be seen to it that too high a concentration of the active substance can impair the consistency of the preparations according to the instant invention. It is also theoretically possible to use the pure active substance in dry powder form as treatment agent for skin diseases; preferably, one will, however, always add an agent which effects the adhesion of the active substance to the skin. Furthermore, disinfecting agents should suitably be added to the preparations in order to prevent the admission of bacteria which reduce the effectiveness of the active substance.

Preparations in the form of solutions are preferably of 20 to 30% concentrations. It is difficult to obtain higher concentrations of the active substance since higher-concentrated solutions have an almost paste-like consistency. Preparations in the form of creams or ointments favorably contain 1 to 10% of the active substance. Thus the overall range is from about 1 to 30% by weight with the balance comprising various carriers.

If required, the preparations can be applied several times daily, even hourly.

The pH value of the preparations according to the invention should lie between about 5 and 9, preferably about 7.5

The invention will be explained by way of the following examples:

EXAMPLE 1

From 10 g of lyophilized standard immune-globulin, by the addition of 490 g Eucerinum anhydricum—pH 7.0—there was prepared an ointment having a pH value of 7.0 with a total weight of 500 g. This ointment, which contains 2.0 g immune-globulin per 100 g, was clinically tested as follows:

| Number of patients | Type of disease | Treatment Time and type | Success rate |
| --- | --- | --- | --- |
| 10 | foot fungus | 1 week - rub well twice daily with salve (altogether about 10 g of | 8/10 = 80% |

-continued

| Number of patients | Type of disease | Treatment Time and type | Success rate |
|---|---|---|---|
| 5 | Herpes simplex (rash on the lip) | 1 week - rub well 3-5 times daily with salve (altogether about 10 g of ointment) | 4/5 = 80% |
| 5 | Herpes zoster (attack on larger skin portions) | 1 week - rub well twice daily with salve (altogether about 20 g of ointment) | 4/5 = 80% |
| 5 | Furuncolosis | 1 week - rub well 3-5 times daily with salve (altogether about 20 g of ointment) | 4/5 = 80% |

*) 2.0 g immune-globulin per 100 g of ointment

EXAMPLE 2

A chemically stabilized immune-globulin (Intraglobulin of Messrs. Biotest-Serum-Institut (GmbH) was dialyzed against $H_2O$ and freeze dried. 25 g of the desalted and freeze dried immune-globulin were processed with 475 g Eucerinum anhydricum—pH 7.0—into a salve. The immune-globulin concentration of this ointment amounted to 5 g per 100 g of ointment. Eucerinum anhydricum is the common name of an ointment base comprising by weight 5% of lanolin alcohol in petroleum jelly, available commercially from Beiersdorf of Germany.

EXAMPLE 3

A chemically stabilized immune-globulin was desalted and freeze dried in the same manner as in Example 2. 25 g of this product were processed with 475 g Eucerinum anhydricum—pH 5.0—and 0.05 g sodium mercurothiolate under sterile conditions into a salve. The immune-globulin concentration of this salve amounted to 5 g per 100 g of ointment.

EXAMPLE 4

10 g of standard immune-globulin were mixed with 90 g Lotio alba aquose, consisting of
zinc oxide:20.0 g
talcum:20.0 g
glycerine:30.0 g
$H_2O$:30.0 g
to produce a thick lotion suited for topical application.

EXAMPLE 5

Non-fractionated serum in the form of a serum confection (commercially available product of Messrs. Biotest-Serum-Institut GmbH "Biseko") was desalted and freeze dried. 50 g of the freeze dried serum were processed together with 450 g Eucerinum anhydricum—pH 7.0—into an ointment. The total protein concentration of the salve amounted to 10 g per 100 g.

During their testing the products of Examples 2 to 4 showed the same good results as set forth for the product of Example 1.

EXAMPLE 6

A 30% hydrophilic ointment according to Deutsches Arzneibuch [German Pharmacopeia], 7th edition, was used for the ointments of Examples 1, 2, 3 and 5 with 70% $H_2O$, which contained 30% cetyl stearyl alcohol, 35% paraffin and 35% Vaseline petroleum jelly.

Especially quick healing successes were obtained with this ointment in case of Herpes-simplex diseases.

It will be appreciated that the instant specification and examples are set forth by way of illustration and not limitation, and that various modifications and changes may be made without departing from the spirit and scope of the present invention.

What is claimed is:

1. A galenic immune-globulin ointment for the treatment of skin fungus diseases, comprising about 1 to 30% by weight of immune-globulin prepared from human blood, and an ointment carrier.

2. A preparation according to claim 1, wherein the immune-globulin has been enzymatically or hydrolytically decomposed.

3. A preparation according to claim 1, wherein the immune-globulin is present as non-fractionated serum.

4. A preparation according to claim 1, having a pH of about 5 to 9.

5. A preparation according to claim 1, in the form of a salve having a concentration of active material of about 1 to 10% by weight and a pH of about 7.

6. A preparation according to claim 5, comprising about 2% by weight of standard immune-globulin, about 5% by weight of lanolin alcohol, and about 93% by weight of petroleum jelly.

7. A preparation according to claim 5, wherein the salve base, exclusive of water, comprises by weight about 30% cetyl alcohol, 35% paraffin and 35% petroleum jelly.

8. A method of treating a patient whose skin is infected by a fungus, which comprises topically applying to the infected area a preparation according to claim 1.

9. A method according to claim 8, in which the immune-globulin is in the form of a salve having a concentration of active material of about 1 to 10% by weight and a pH of about 7.

* * * * *